United States Patent [19]

Mares et al.

[11] 4,171,313

[45] Oct. 16, 1979

[54] MOLYBDENUM AND TUNGSTEN PEROXO COMPLEXES USEFUL AS OXIDATION CATALYSTS

[75] Inventors: Frank Mares, Whippany; Stephen E. Jacobson, Randolph; Reginald T. Tang, Bridgewater, all of N.J.

[73] Assignee: Allied Chemical Corporation, Morris Township, Morris County, N.J.

[21] Appl. No.: 842,130

[22] Filed: Oct. 14, 1977

[51] Int. Cl.$^2$ .................. C07D 309/30; C07D 313/04; C07C 69/66; C07C 59/04
[52] U.S. Cl. .............................. 260/343; 260/343.5; 260/586 P; 260/596; 546/5; 560/179; 562/579; 568/860; 423/584; 252/430; 252/431 C
[58] Field of Search ............... 260/343, 343.5, 535 R; 560/179; 562/579

[56] References Cited

U.S. PATENT DOCUMENTS

| | | | |
|---|---|---|---|
| 3,428,656 | 2/1969 | Weiss et al. | 260/343 |
| 3,584,011 | 6/1971 | Weiss et al. | 260/343 |
| 3,681,395 | 8/1972 | Mookherjee | 260/343 |
| 3,728,358 | 4/1973 | Mookherjee | 260/343 |
| 3,833,613 | 9/1974 | Field et al. | 260/343 |

OTHER PUBLICATIONS

Fieser & Fieser, pp. 456–467, John Wiley and Sons Inc.

*Primary Examiner*—Natalie Trousof
*Assistant Examiner*—Jane T. Fan
*Attorney, Agent, or Firm*—Horst M. Kasper; Robert A. Harman

[57] ABSTRACT

A catalytic system for oxidation of organic compounds including olefins, cyclic ketones and secondary alcohols. Soluble peroxo or solid supported oxo or peroxo complexes of molybdenum or tungsten are used in the presence of hydrogen peroxide to effect the oxidation. The resulting products include lactones, hydroxy acids, ketoacids, hydroxy esters and ketoesters from cyclic ketones; ketones from secondary alcohols and polyols or derivatives thereof from allylic alcohols.

31 Claims, No Drawings

MOLYBDENUM AND TUNGSTEN PEROXO COMPLEXES USEFUL AS OXIDATION CATALYSTS

BACKGROUND OF THE INVENTION

It is known that secondary alcohols can be oxidized to ketones and cyclic ketones can be oxidized to lactones, hydroxy acids and their derivatives. For example, secondary alcohols can be oxidized by peracids in the presence of strong acids or nitroxides as catalysts. Peracids also oxidize cyclic ketones to lactones or to hydroxy acids in the Baeyer-Villiger reaction. Peracids, persulfuric, perbenzoic, perphthalic, peracetic, and trifluoroperacetic acids may be employed. In some instances peracids can be substituted by concentrated (90%) $H_2O_2$ and carboxylic acid anhydride. In all the above processes the main disadvantage is the fact that $H_2O_2$ alone will not react and that the necessity to use either peracid or a mixture of an excess of acid anhydride with concentrated (90%) $H_2O_2$ cannot be avoided. Peracids are relatively expensive since they have to be prepared either by oxidation of aldehydes, or by a reaction of acid anhydrides with concentrated (90%) $H_2O_2$, or from $H_2O_2$ and carboxylic acid according to a tedious process where $H_2O$ is removed by azeotropic distillation. Also, separation of carboxylic acid formed from peracid and the oxidation products may present difficulties. Similarly, peracids have been used to oxidize olefinic double bonds to an epoxide. Allan et al. in U.S. Pat. No. 3,156,709 of Nov. 10, 1964 disclose the oxidation of an olefinic compound with hydrogen peroxide in the presence of catalysts which are inorganic compounds of metals such as osmium, tungsten, vanadium, molybdenum, uranium, niobium, chromium, tantalum, selenium, cerium, ruthenium, titanium, zirconium and thorium forming an insoluble organic compound.

Mimoun in German Pat. No. 1,815,998 issued Dec. 4, 1969 discloses organic peroxide compounds of molybdenum and tungsten, their preparation and their use in the epoxidation of olefinic double bonds by hydrogen peroxide. The organic compounds of molybdenum and tungsten disclosed are peroxide complexes with a carboxylic acid amide and with amides of mineral acids.

Bocard et al. in the French Patent No. 2,082,811 disclose additional metal peroxo complexes containing as organic ligands oxides of pyridine and heterocyclic nitrogen compounds bound to molybdenum and tungsten for the epoxidation of olefins with hydrogen peroxide. Ferruccio in Italian Patent No. 919,509 issued Mar. 15, 1972 discloses the utilization of an 8-hydroxy quinoline molybdenum complex as a catalyst for the oxidation of olefinic double bonds with hydrogen peroxide.

One disadvantage of the prior art in epoxidation with $H_2O_2$ is the efficiency in the use of $H_2O_2$ for oxidation of olefins to epoxides or diols or diol derivatives. Usually a substantial part of $H_2O_2$ is decomposed to $H_2O$ and $O_2$.

Peroxy molybdate derivatives of organic bases are disclosed by R. G. Beiles and E. M. Beiles in *Russian Journal of Organic Chemistry*, Vol. 12, No. 4, page 467 (1967). Beiles et al. describe the preparation of complexes of molybdenum and picolinic acid in a sulfuric acid solution and depending upon the relative amount of the reagents used the resulting complexes have 1,2, and 3-amine molecules per molecule of $H_2MoO_6$.

Westlake et al. report in *C.R. Acad. Sc. Paris*, Vol. 280, Series C, page 113 (1975) the preparation of dipicolinic acid complexes of peroxo molybdates and tungstates in an acid medium adjusted by addition of sulfuric acid.

Kerogat et al. in *Journal of Fluorine Chemistry* 6, 67–75 (1975) further react the dipicolinic acid complexes of peroxo molybdates and tungstates with a stoichiometric amount of fluoride in acetonitrile.

SUMMARY OF THE INVENTION

A process is provided for preparing catalysts comprising peroxo complexes of molybdenum or tungsten with picolinic or dipicolinic acid by dissolving the metal oxide in hydrogen peroxide, and adding a complexing aza-2-carboxylic acid heterocyclic compound to the dissolved metal oxide.

This invention is directed to an oxidation process wherein the oxidizing agent is hydrogen peroxide and the oxidation is catalyzed by peroxo complexes of molybdenum or tungsten and the improvement comprises employing a peroxo complex soluble in the oxidation reaction mixture wherein molybdenum or tungsten atoms are connected to a complexing aza acid heterocyclic compound having a carboxylic acid group on a carbon atom which is in α-position relative to the aza nitrogen, preferably picolinic or dipicolinic acid. Cyclic ketones and secondary alcohols are oxidized with the agent hydrogen peroxide wherein the oxidation is catalyzed by any covalent peroxo complex of molybdenum or tungsten. The preferred catalyst for oxidation of cyclic ketones or secondary alcohols are a picolinate, dipicolinate, aza, or carboxylate of peroxo complex of molybdenum or tungsten. Olefins containing hydroxy, carboxy or ester groups are oxidized by hydrogen peroxide wherein the improvement comprises the use of peroxo complexes of molybdenum and tungsten containing aza acid heterocyclic ligands having a carboxylic acid group on a carbon atom which is in α-position relative to the aza nitrogen.

An improved catalyst is provided by supporting on a catalyst carrier any of the covalent picolinate, dipicolinate, aza, carboxylate, 2,6-bishydroxymethylpyridine, oxo, peroxo or aza-α-carboxylic acid heterocyclic complexes of molybdenum or tungsten.

A process for oxidation with hydrogen peroxide is disclosed with catalysts including peroxo complexes of molybdenum or tungsten wherein the complexes are supported on a catalyst carrier, preferably as picolinates or dipicolinates.

A stabilizer for aqueous hydrogen peroxide is provided by complexes of the aza-α-carboxylic acid derivatives of heterocyclic molecules preferably, the picolinates and dipicolinates of molybdenum and tungsten peroxo complexes.

The following compounds are disclosed wherein M is molybdenum or tungsten:

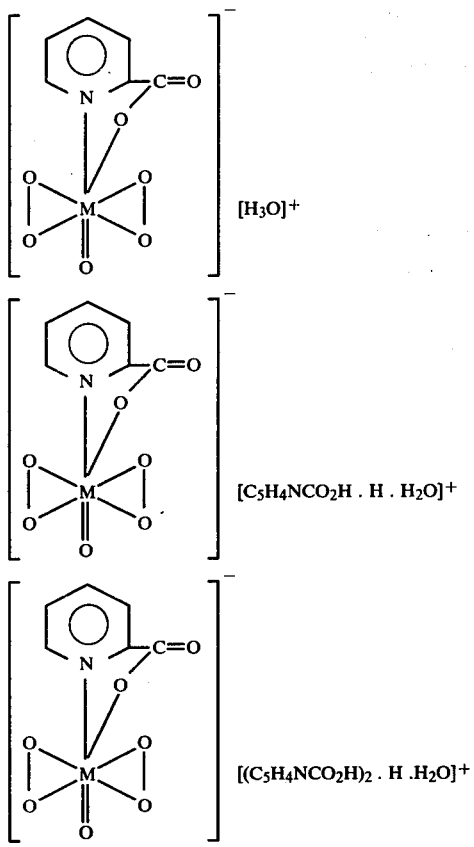

$MO_2$(2,6-bishydroxymethylpyridine bisalcoholate); and $MO_5$(2,6-bishydroxymethyl pyridine).

DETAILED DESCRIPTION OF THE INVENTION

It has now been found that in accordance with our invention the oxidation of secondary alcohols and ketones with hydrogen peroxide can be catalyzed by organic peroxo complexes of molybdenum or tungsten. Such peroxo catalysts include $MO_5(L)(OH_2)/M=Mo$, W; L=N,N,N-hexamethyl phosphoramide, 2,6-bishydroxymethylpyridine, dimethyl formamide, ketone, etc. and $MO_5L_1L_2/M=Mo$, W; $L_1$=N,N,N hexamethylphosphoramide, dimethyl formamide, ketone; $L_2$=pyridine, N,N,N-hexamethylphosphoramide, dimethyl formamide, dimethylsufoxide, ketone, etc. or wherein $L_1$ and $L_2$ represent a polydentate ligand.

Suitable catalysts include those oxo complexes which are oxidized with hydrogen peroxide to peroxo complexes of molybdenum or tungsten, e.g. $MO_2$ (2,6-bishydroxy methylpyridine bisalcoholate) with M=Mo, W for in situ formation of the active ingredient. Oxo and peroxo complexes of tungsten frequently have an analogous formula corresponding to that of a molybdenum complex.

In accordance with our invention the preferred complexes are essentially seven fold coordinated complexes of molybdenum and tungsten wherein the metal center is coordinated to at least one aza group, one carboxyl group and one peroxo group. They are useful catalysts for the oxidation with hydrogen peroxide of olefins to epoxides or derivatives thereof, of ketones to lactones, or derivatives thereof and of secondary alcohols to ketones. Preferably the aza group and the carboxyl group form together with the metal atom a 5-membered ring comprising the metal atom, the nitrogen atom, a carbon atom of the aromatic ring, a carbon atom of the carboxyl group and an oxygen atom of the carboxyl group. The most preferred complexes of the present invention have two such hetero rings comprising the same type of atoms and having a joined edge in the metal-nitrogen bond. Four coordination positions of the metal being occupied by the aza nitrogen, the oxygen from a carboxyl group and by a peroxo group, the remaining three positions can be occupied by monovalent or bi-valent electro-negative groups such as halogen, oxygen, peroxy, hydroxy. In general, a complex arises which is essentially neutral or has not more than one positive or negative charge. In particular, one of the named three remaining coordinated positions around the metal atom can be occupied by an electron donor such as the oxygen in a ketone, water, N,N,N-hexamethyl phosphoramide or alcohol, or an olefinic double bond. The four members nitrogen, carbon, carbon and oxygen of the heterocyclic five membered ring can be provided by derivatives of picolinic acid such as methyl, nitro, halogen, carboxyamide, carboxyl, phenyl, and hydroxy substituted picolinic acid. A rational name for picolinic acid is pyridine 2-carboxylic acid. Such derivatives of picolinic acid include but are not limited to 4,6-dihydroxypicolinic acid, 4,6-diethoxypicolinic acid, 6,7-dihydroxy-isoquinoline-1-carboxylic acid, 1,4-dihydroxyisoquinoline-3-carboxylic acid, 1,4-dihydroxy-7-methylisoquinoline-3-carboxylic acid, 4,5,6-trihydroxypyridine-2-carboxylic acid, 6-hydroxypyridine-2,3-dicarboxylic acid, 4-hydroxydipicolinic acid, 3,5-dichloro-4-hydroxydipicolinic acid, 3,5-dibromo-4-hydroxydipicolinic acid, 6-hydroxy-4-methylpyridine-2,3-dicarboxylic acid, 3-acetylpicolinic acid, 3-benzoylpyridine-2-carboxylic acid, 3-p-tolyl-pyridine-2-carboxylic acid, 3-[4-carboxybenzoyl]-picolinic acid, 3-[2-carboxyphenyl]pyridine-2-carboxylic acid, 6-methyl-3-[2-carboxyphenyl]pyridine-2-carboxylic acid, 6-methyl-4-phenylpyridine-2,3-dicarboxylic acid, 4,6-dimethyl-3-[2-carboxyphenyl]pyridine-2-carboxylic acid, 7,8-benzoquinoline-2,4-dicarboxylic acid, 5,6-benzoquinoline-2,4-dicarboxylic acid, 4-phenylquinoline-2,3-dicarboxylic acid, 4,6-diphenylquinolinic acid, pyridine-2,3,4-tricarboxylic acid, pyridine-2,3,6-tricarboxylic acid, pyridine-2,4,5-tricarboxylic acid, pyridine-2,4,6-tricarboxylic acid, 3,5-dibromopyridine-2,4,6-tricarboxylic acid, 4-methylpyridine-2,3,6-tricarboxylic acid, quinoline-2,3,4-tricarboxylic acid, 6-phenylpicolinic acid, 5,6-benzoquinolinic acid, pyridine-2,3-dicarboxylic acid [quinolinic acid], pyridine-2,4-dicarboxylic acid, pyridine-2,5-dicarboxylic acid, dipicolinic acid having the rational name pyridine-2,6-dicarboxylic acid, 4-chloropyridine-2,6-dicarboxylic acid, 4-methylquinolinic acid, 6-chloro-4-methylpyridine-2,3-dicarboxylic acid, 6-methylpyridine-2,4-dicarboxylic acid, 4-methyl-5-ethylpyridine-2,3-dicarboxylic acid, 6-chloro-4-methyl-5-ethylpyridine-2,3-dicarboxylic acid, 4,5,6-trimethylpyridine-2,3-dicarboxylic acid, quinoline 2,3-dicarboxylic acid [acridinic acid], quinoline-2,4-dicarboxylic acid, quinoline-2,6-dicarboxylic acid, isoquinoline-1-carboxylic acid.

The preferred complexing agents of the present invention include picolinic and dipicolinic acid. The complexes of the present invention can be prepared either in situ during the catalytic reaction or in advance beforehand. In general, such a complex is prepared by reacting a metal oxide of tungsten and molybdenum with hydrogen peroxide and the aza carboxyl compound. It is convenient to dissolve initially the molybdenum trioxide or tungstic acid with hydrogen peroxide in an aqueous solution at a non critical temperature range for sufficient time for preparation of the peroxide complex. To the solution obtained is added the ligand having an aza and a carboxy group. It is preferred not to add sulfuric acid, since the additions may decrease the yield. Preferably, molybdenum trioxide or tungstic acid are reacted at about 45° to 50° C. for 4 hours with hydrogen peroxide to give a soluble metal peroxo complex and this complex is then reacted with picolinic acid or dipicolinic acid. The resulting complexes can be precipitated or crystallized by conventional techniques such as cooling or adding a cosolvent or by evaporating the solvent under reduced pressure. The preferred catalysts of the present invention are soluble in the oxidation reaction mixture. The reaction mixture can comprise organic solvents with freezing points below 10° C.

The complexes formed by picolinic acid include

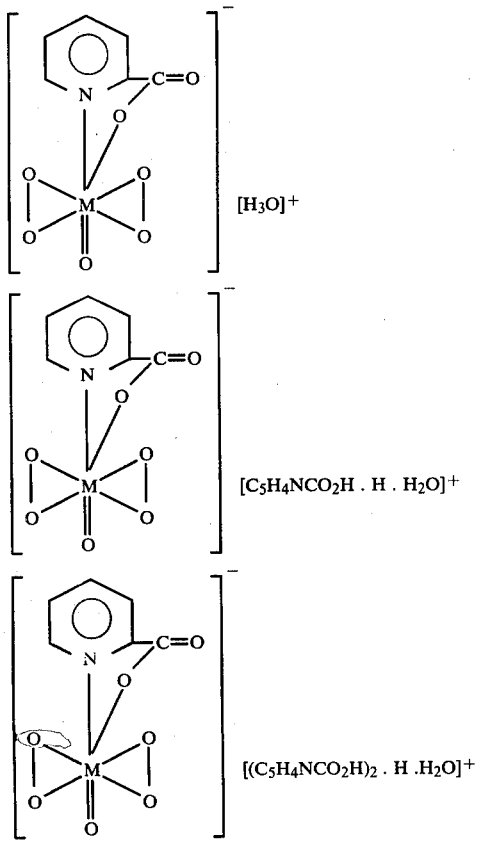

wherein M represents either molybdenum or tungsten. It has been found that the preferred catalysts of the present invention act as stabilizers against the decomposition of aqueous hydrogen peroxide solutions.

The tungsten and molybdenum complexes of the present invention can be used to catalyze the oxidation of olefins to diols or derivatives thereof. Olefins useful include those having hydroxy, carboxyl or ester groups. Preferred are olefinic alcohols having the hydroxy group on a carbon atom adjacent to the double bond. Such olefins comprise allyl alochol, crotyl, alcohol, 1-butene-4-ol, 2-pentene-1-ol, 2-heptene-1-ol, 1-octene-3-ol, 2-cyclohexenol, 2-cyclopentenol, acrylic acid, methacrylic acid, 2-pentenoic acid, 3-hexenoic acid, 2-octenoic acid, 2-cyclopentenyl acetic acid, 1-cyclohexyl acrylic acid, and their hydroxy, alkyl, halide, nitrilo and ester derivatives, e.g. methyl acrylate. Preferred olefins comprise such olefins which have a hydroxy group on the carbon atom adjacent to the double bond such as an allyl alcohol. Di- and triolefins can also be oxidized according to the present invention. Di- and triolefins useful include e.g. 2,4-hexadienol and hydroxy, halide and alkyl derivatives thereof. Preferred are diolefins having a hydroxy group on a carbon atom adjacent to the double bond.

The oxidations of the olefins can be achieved by diluting the reactants of olefins, aqueous hydrogen peroxide and the molybdenum or tungsten complex with a suitable solvent and reacting them at a suitable temperature for sufficient time. One advantage of the invention is the efficiency in the use of hydrogen peroxide. The concentration of the hydrogen peroxide in water is not critical but above a 30% to 90% concentration of hydrogen peroxide in water are appropriate. Usually a slight excess of the amount of hydrogen peroxide present is employed over the amount required for stoichiometric oxidation. The amount of molybdenum catalyst present would ideally not be critical at all. However, catalyst amount of a molar ratio of between 1 to 10 and 1 to 100 in relation to the amount of olefin has been found to be preferred. The amount of solvent present is not critical but a range of between 2 times and 20 times the weight of the olefin is preferred. The solvents useful in the present invention include, but are not limited to, methanol, acetonitrile, ethyl ether, propyl ether, chlorinated hydrocarbons with up to 7 carbon atoms and their mixtures. The reaction temperature for the oxidation is not critical but a temperature between 60° C. and 90° C. is preferred. The reaction time depends on the reaction temperature and usually an overnight reaction of about 24 hours is involved.

The tungsten and molybdenum peroxo complexes of the present invention are useful in catalyzing the oxidation of cyclic ketone to hydroxy acids and lactones. The starting cyclic ketone and the catalysts are diluted with a suitable solvent and hydrogen peroxide is added. After reacting the mixture for a sufficient time the oxidation product is formed. The catalysts useful include the molybdenum and tungsten peroxo catalysts disclosed in the present invention. Starting ketones include essentially saturated cyclic ketones. Unsaturated cyclic ketones can also be employed but there may occur the oxidation of the double bond at the same time. Among the saturated ketones useful in the present invention are included cyclopentanone, cyclohexanone, cyclopentadecanone, camphor, fenchone, 2-phenyl cyclohexanone, 2-phenyl cyclopentanone, 2-chlorocyclohexanone. Unsaturated ketones are subject to both oxidation of the ketone group and oxidation of the double bond. Such unsaturated ketones include 3-cyclohexenone, 3-cyclopentenone, 4-methyl-3-cyclohexenone, 2-methyl-3-cyclohexenone, 2-phenyl-3-cyclohexanone. Preferred ketones include cyclohexanone, 2-methylcyclohexanone, and cyclopentanone for the formation of cyclic lactones.

The diluting solvent can be chosen among a number of solvents including, but not limited to, acetonitrile, ether, dioxane, tetrahydrofuran, propionitrile, methanol, chlorinated hydrocarbon, chloroform, acetic acid, formic acid and mixtures thereof. The presence of water favors formation of hydroxy carboxylic acids compared to lactones. Preferred solvents include methanol, acetonitrile, and propionitrile. The presence of methanol results in the formation of methyl esters of hydroxy carboxylic acids. The mol ratio of ketone to a catalyst applied lies in the range of about 100:1 to 1:1 with a preferred molar ratio of about 100:1 to 10:1. The weight ratio of solvents to ketone include the range of about 0 to 10:1. To the solution obtained, hydrogen peroxide is added. This addition in general proceeds slowly. The amount of hydrogen peroxide added depends on the desired final product. For instance, if one desires to obtain a lactone hydroxy acid or its ester, then it is suitable to employ stoichiometric amounts of hydrogen peroxide relative to the amount of ketone available. In case e.g. ketoester is the desired product; 2 equivalents of hydrogen peroxide are required.

The concentration of the hydrogen peroxide is not critical. A preferred concentration lies in the range of 30% to 90% hydrogen peroxide in water.

The reaction temperature is not critical, but a preferred range is 60° to 90° C. The reaction time depends on the reaction temperature. It was convenient to react the materials overnight and to employ a reaction time of approximately 24 hours. An internal standard can be used to determine the end of the reaction by chromatographic analysis. Internal standards include but are not limited to biphenyl.

The catalysts of the present invention are useful in the oxidation of secondary alcohols to ketones. The secondary alcohol, the solvent and the catalyst are added together and agitated. Hydrogen peroxide is added to this solution and then the materials are reacted at an appropriate temperature for sufficient time. In general, the amount of the alcohol to the catalyst lies in the range of about 100:1 to 1:1 with the preferred ratio 100:1 to 10:1. The secondary alcohols useful in the present invention include but are not limited to 2-propanol, 2-butanol, 2-pentanol, 3-pentanol, 2-octanol, 3,9-diethyl-6-tridecanol, cyclohexanol, cyclopentanol, phenethyl alcohol, alpha-phenetol, 5-hydroxycaproic acid, menthol, 6-hydroxyheptanoic acid. Suitable solvents for the catalyst and the secondary alcohol include methanol, acetonitrile, dioxane, trichloroethylene, chloroform, etc. The molar ratio between solvent and secondary alcohol can include the range of 0 to 100 to 1. Generally, a small excess of alcohol is employed. The employed hydrogen peroxide may be a 30 to 90% hydrogen peroxide solution in water. The reaction temperature is not critical. A preferred range of the reaction temperature is between about 60° C. and 90° C. The reaction time has to be sufficient to achieve reaction. In general such times are about 2 to 24 hours.

It was found that the preferred catalyst for the oxidation of secondary alcohols are tungsten picolinates. In the case where 1 mole of hydrogen peroxide is used for 1 mole of alcohol, the product is essentially the corresponding ketone.

For cyclic ketones molybdenum and tungsten dipicolinate are preferred catalysts. Employing only 1 mole of hydrogen peroxide per mole of ketone then the ketone is preferentially oxidized even though secondary alcohols may be present.

The process of the present invention preferentially reacts hydrogen peroxide with olefins, compared to a reaction with secondary alcohols and ketones. Oxidation can be limited to olefins even in the presence of secondary alcohols and ketones when an amount of hydrogen perioxide is employed which is stoichiometric relative to the amount of olefin present in the reaction.

The methods of use of the catalysts of the present invention include not only the above discussed homogeneous catalysts but also heterogeneous catalysts, preferably in the gas phase. The complex catalysts disclosed above are supportable on a solid. In general the solids suitable as carriers have to be chemically inert. Useful catalyst carrier materials include natural clays, bauxites and diatomacious earths, sintered substrates from salts such as nitrates, chromates, tungstates, molybdates, manganates, vanadates, oxides and carbonates, impregnated and sintered material such as alumina impregnated with a molybdate or tungstate solution, and precipitated and dried catalytic substrates, pumice, porcelain, asbestos, alumina, glass, quartz, kaolin, silicates, infusorial earth, magnesium and barium sulfates, molybdates and tungstates, zeolite magnesia and magnesium carbonate. Preferred catalyst carriers are formed by flux calcination of zeolite diatomateous silicates such as disclosed by D. M. Ottenstein in U.S. Pat. No. 3,542,584 issued Nov. 24, 1970.

The catalyst is combined with the catalyst carrier. Preferably the catalyst carrier is impregnated with a solution of the catalyst in a suitable solvent. A preferred range of catalyst relative to the carrier is about 1% to 5%. The supported catalyst is then introduced in a reaction chamber. A flow of a ketone or secondary alcohol possibly diluted with one of the named solvents is introduced into the reaction chamber together with hydrogen peroxide contained in the solution or from a separate source. These reaction materials can be introduced in liquid form, in vapor form or in combination with a carrier gas. The choice of procedure depends on the volatility of the components and with less volatile components being introduced into the reaction chamber either in liquid form or combined with an inert carrier gas. Such inert or oxidizing carrier gases include argon, helium, neon, nitrogen, oxygen, carbon dioxide, and mixtures thereof. In case an oxidizing gas is employed explosive mixtures have to be avoided.

The concentrations are not critical for the heterogeneous catalytic oxidation of ketones and secondary alcohols, but they have to be such that suitable reaction mixtures outside of flammable limits result. Preferably ketones would be fed into the reactor directly and $H_2O_2$ in a solution at 10-20% concentration. Solvents for $H_2O_2$ include but are not limited to the ketone being oxidized, acetonitrile and propionitrile. For lactone formation the presence of water is undesirable because of possible hydrolysis. The reaction temperature for the heterogenous catalysis of oxidation in the gas phase is not critical, preferred are temperatures of about between 100° C. and 200° C. More preferred is a temperature range of about between 125° C. and 170° C.

EXAMPLE 1

Preparation of complex $[H_3O^+][MoO_5(\text{picolinate})]^-$ 15 g molybdenum trioxide was dissolved in 150 ml of 30% hydrogen peroxide at 40° to 45° C. overnight. The solution obtained was cooled to 0° C. and 12.8 g picolinic acid dissolved in 20 ml of water was slowly added. Within ½ to 1 hour, 28 g of a light yellow precipitate of $[H_3O^+][MoO_5(\text{picolinate})]^-$ was obtained with 86% yield. Analysis calculated for $[MoO_5(C_5H_4NCOOH)]^-[H_3O]^+$: C, 22.72; H, 2.23; N, 4.42; O [active] 20.24; Mo, 30.26; found: C, 23.14%; H, 2.42%; N, 4.23%; O [active], 19.81%; Mo, 29.67%. Infrared analysis $[CO]=1685$ cm$^{-}$ [very strong]; $[OH]=3480$ cm$^{-1}$ [very strong, broad]; $[O-O]=850$, 865 cm$^{-1}$ [very strong]; $[Mo=O]=960$, 975 cm$^{-1}$ [very strong].

EXAMPLE 2

Preparation of $MoO_3[H_2O][dipicolinate]$ 18 g of molybdenum trioxide was dissolved in 300 ml of 30% hydrogen peroxide at 40° to 45° C. overnight. The solution was heated to 60° C. and 18 g solid dipicolinic acid, was added. The solution turned from bright yellow to orange in a few minutes. After continued stirring for 8 hours at 60° C., the reaction mixture was cooled and the orange precipitate was filtered. The precipitate was then extracted with 50 ml anhydrous methanol and the resulting solution was filtered whereby a white solid of dipicolinic acid was left on the filter paper. The volume of the filtrate was decreased to 20 ml and then the filtrate was cooled to 0° C. and orange crystals of $MoO_3[H_2O]$ [dipicolinate] was precipitated. After filtration, the amount of product was 21 g corresponding to a 47% yield.

Analysis: calculated for $C_7H_5MoNO_8$: Mo, 29.33%; O [active], 10.25%; N, 4.28%; C, 25.71%; H, 1.54%. Found: Mo, 29.64%; O [active], 9.63%; N, 4.23%; C, 26.03%; H, 1.72%. Infrared analysis: $[CO]=1700$ cm$^{-1}$ [strong, broad]; $[O-O]=900$ cm$^{-1}$ [strong]; $[Mo=O]=970$ cm$^{-1}$ [strong].

EXAMPLE 3

Preparation of $[MoO_5(picolinate)]^{-}[(picolinic\ acid)_2.H(H_2O)]^{+}$ 5 g of molybdenum trioxide was dissolved in 50 ml of 30% hydrogen peroxide at 40° to 45° C. overnight. The solution was cooled with an ice bath to 0° C. and 12.8 g of picolinic acid dissolved in 15 ml of water was added. After 10 minutes the solution was removed from the ice bath and the solution was stirred at room temperature. After 1½ hours, a bright yellow precipitate, 13.6 g, was obtained in a yield of 75%. The recovered solid was washed well with ether. It was possible to recrystallize the yellow solid from 30% concentrated hydrogen peroxide.

Analysis: calculated for $MoO_{12}N_3C_{18}H_{17}$: C, 38.38%; H, 3.04%; N, 7.46%; Mo, 17.03%. Found: C, 38.41%; H, 3.26%; N, 7.39%; Mo, 17.05%. Infrared spectrum: $[CO]=1655$ cm$^{-1}$ [strong]; $[OH]=3440$ cm$^{-1}$, 3250 cm$^{-1}$ [medium, broad]; $[O-O]=860$ cm$^{-1}$ [very strong]; $[Mo=O]=935$ cm$^{-1}$ [very strong].

EXAMPLE 4

Preparation of $[MoO_5(picolinate)]^{-}[picolinic\ acid.H(H_2O)]^{+}$ 5 g of molybdenum trioxide was dissolved in 30 ml of 30% hydrogen peroxide at 40° to 45° C. overnight. The resulting solution was cooled with ice to 0° C. and 8.6 picolinic dissolved in 10 ml of water was added. After an hour of stirring at room temperature, a bright yellow solid precipitated from solution (7 g, 47%.) This solid was recrystallized from 30% hydrogen peroxide.

EXAMPLE 5

Preparation of $[MoO_5(picolinate)]^{-}[picolinic\ acid.H(H_2O)]^{+}$ 1 g of the complex $[MoO_5(picolinate)]^{-}[(picolinic\ acid).H(H_2O)]^{+}$ was stirred in methanol at room temperature overnight. A yellow solid precipitated and filtering the next morning gave 0.35 g or 44% yield. Analysis: the yellow solid of Example 4 and 5 were analyzed for $[MoO_5(picolinate)]^{-}[picolinic\ acid.H(H_2O)]^{+}$. Analysis calculated for $MoO_9N_2C_{12}H_{10}$: C, 34.12%; H, 2.39%; N, 6.63%; Mo, 22.75%. Found: C, 34.06%; H, 2.48%; N, 6.55%; Mo, 23.46%. Infrared analysis: $[CO]=1720$ cm$^{-1}$ [strong, broad]; $[O-O]=850$ cm$^{-1}$ [very strong]; $[M=O]=955$ cm$^{-1}$ [very strong]. The analogous tungsten compound $[WO_5(picolinate)]^{-}[picolinic\ acid.\ H(H_2O)]$ can be prepared analogously from $[WO_5(picolinate)]^{-}[(picolinic\ acid)_2H.(H_2O)]^{+}$.

EXAMPLE 6

Preparation of $[MoO_5(picolinate)]^{-}[methyl\ picolinate.H]^{+}$ 1 g of the complex $MoO_5(picolinate]^{-}[H_3O]^{+}$ was dissolved in 10 ml of methanol and stirred at room temperature for one hour. 0.4 g of a bright yellow solid precipitated from solution at this time and a yield of 29% was obtained. Analysis calculated for $MoO_9N_2C_{13}H_{12}$: C, 35.78%; H, 2.78%; N, 6.42%; O [active], 14.75%; Mo, 22.00%. Found: C, 35.79%; H, 2.90%; N, 6.26%; O [active] 14.11%; Mo, 22.23%. Infrared analysis: $[CO]=1745$ cm$^{-1}$ [strong], 1680 cm$^{-1}$ [strong]; $[O-O]=845$ cm$^{-1}$ [strong], 855 cm$^{-1}$ [strong]; $[Mo=O]=945$ cm$^{-1}$ [strong]. Nuclear magnetic resonance $[C_5ND_5]$: 4.40, singlet, 3H, $[C(O)OCH_3]$; 8.2–10.4, multiplet, 8H, $[C_6H_4NCO_2]$.

EXAMPLE 7

Preparation of $MoO_3[dipicolinate][HMPA]$ 1 g $MoO_3[dipicolinate][H_2O]$ was dissolved in 50 ml tetrahydrofuran, 0.55 g N,N,N-hexamethylphosphoramide (HMPA) was slowly added and an orange precipitate immediately formed. After filtration, 1.2 g of the precipitate was obtained which is equivalent to a 79% yield. Analysis calculated for $MoO_8N_4C_{13}H_{21}P$: C, 32.02%; H, 4.35%; N, 11.48%; Mo, 19.50%. Found: C, 32.01%; H, 4.43%; N, 11.27%; Mo, 19.02%. Infrared analysis: $[CO]=1700$ cm$^{-1}$ [very strong]; $[O-O]=895$ cm$^{-1}$ [strong]; $[Mo=O]=950$ cm$^{-1}$ [strong].

EXAMPLE 8

Preparation of $MoO_2[2,6$-bishydroxymethylpyridine bisalcoholate]

1.06 g of molybdenum trioxide and 1.05 g of 2,6-bishydroxymethylpyridine were mixed and refluxed with 10 ml of water for 8 hours. A 100% yield of the molybdenum complex was obtained after filtration, water washing, and drying under vacuum.

Analysis calculated for $C_7H_7NO_4Mo$: C, 31.71%, H, 2.67%, N, 5.28%, Mo, 36.19%. Found: C, 31.06%, H, 2.75%, N, 4.94%, Mo, 38.1%. Infrared analysis: no absorption bands characteristic of [OH], [CO], and $[O-O]$; $[Mo=O]=870$ cm$^{-1}$ [strong].

EXAMPLE 9

Preparation of $MoO_5(2,6$-bishydroxymethylpyridine)

2 g of $MoO_3$ were dissolved in 17 ml of 30% hydrogen peroxide at 40°–45° overnight. 1.94 g of the ligand 2,6-bishydroxymethyl pyridine were added and stirred at room temperature, forming a yellow precipitate. The solid, the desired product in 70% yield, was isolated by filtration followed by washing with water and drying under vacuum. Analysis calculated for $C_7H_9NO_7Mo$: C, 26.68%; H, 2.88%; N, 4.45%. Found: C, 26.50%; H, 2.95%; N, 4.11%. Infrared analysis: no absorption bands characteristic of [C=O]; [OH]=3350 cm$^{-1}$ [broad], [O—O]=860 cm$^{-1}$ [very strong], [Mo=O]=955 cm$^{-1}$ [very strong].

The same complex was also prepared from the corresponding di-oxo complex $MoO_2$(2,6-bishydroxymethylpyridine bisalcoholate) with hydrogen peroxide. Thus, when 1 ml of 30% hydrogen peroxide in acetonitrile was added to 0.20 g of $MoO_2$[2,6-bishydroxymethylpyridine bisalcoholate], a color change to yellow was observed. After heating at 50° for 20 hr., the resulting yellow solid was filtered, washed with methanol and ether, and dried under vacuum. The product, in 75% yield, exhibited identical infrared absorption bands to that obtained in the above preparation.

EXAMPLE 10

Preparation of $MoO_3$[diethylenetriamine]

This complex was prepared according to the procedure given in W. F. Marzluff, Inorganic Chem., 3, 395 (1964), from molybdenum trioxide and diethylenetriamine. The white crystalline product was obtained in comparable yield and exhibited identical infrared absorption bands.

EXAMPLE 11

Preparation of $MoO_5$[HMPA][$H_2O$] and $MoO_2$[acetylacetonate]$_2$

A method for preparation of $MoO_5$[HMPA][$H_2O$] as described in H. Mimoun, I. S. de Roch and L. Sajus in Bull. Soc. Chim. France 1481 (1969) was employed. An equimolar quantity of HMPA was added to a $MoO_3$—$H_2O_2$ (30%) solution to precipitate the yellow solid $MoO_5$[HMPA][$H_2O$].

A method for preparing Mo(O)$_2$[acetylacetonate]$_2$ is described in H. Zelwke Jr. and J. Veal, Inorganica Chim. Acta 3 623 (1969).

EXAMPLE 12

Preparation of [$H_3O$]$^+$[$WO_5$(picolinate)]$^-$ 15 g tungstic acid $WO_3.H_2O$ was heated at about 40° to 50° C. in about 75 ml of 30% hydrogen peroxide for 24 hours. 7.4 g of picolinic acid was dissolved in 10 ml of water. After cooling the tungstic acid solution with ice to 0° C., the picolinic acid solution was slowly added. The resulting solution was stirred overnight at room temperature. The volume of the solution was reduced to 30 ml until the product, a white solid (15 g, 74% yield), precipitated. An analogous reaction was tried with tungsten trioxide $WO_3$, but no complex was formed under these conditions. Analysis: calculated for $WO_8NC_6H_7$: C, 17.84%; H, 1.75%; N, 3.45%; W, 45.41%. Found: C, 17.85%; H, 1.98%; N, 3.41%; W, 44.74%. Infrared analysis: [CO]=1690, 1695 cm$^{-1}$ [very strong]; [OH]=3450 cm$^{-1}$ [very strong, broad]; [O—O]=825, 835, 845 cm$^{-1}$ [very strong]; W=O]=980 cm$^{-1}$ [very strong].

EXAMPLE 13

Preparation of complex [$WO_5$(nicotinate)]$^-$[$H_3O$]$^+$ 5 g tungstic acid $WO_3.H_2O$ was stirred at about 45° C. in 75 ml of 30% hydrogen peroxide overnight. After cooling the solution to room temperature, 2.46 g nicotinic acid partially dissolved in 20 milliliters of water was added. The nicotinic acid gradually dissolved in the hydrogen peroxide solution. The solution was stirred at room temperature for 3 hours and then evaporated to ⅓ at its original volume. The solution stood several hours at room temperature until white crystals of [$WO_5$(nicotinate)]$^-$[$H_3O^+$] precipitated from the solution. 7 g of the complex [$WO_5$(nicotinate)]$^-$[$H_3O^+$] was collected which corresponds to an 85% yield. Analysis: calculated for $WO_8NC_6H_7$: C, 17.84; H, 1.75%; N, 3.47%; W, 45.56%. Found: C, 18.06%; H, 1.86%; N, 3.52%; W, 44.5%. Infrared analysis: [CO]=1680 cm$^{-1}$ [strong, broad]; [O—O]=830 cm$^{-1}$ [strong]; W=O]=955 cm$^{-1}$ [strong].

EXAMPLE 14

Preparation of [$WO_5$(picolinate)]$^-$[(picolinic acid)$_2$.H($H_2O$)]$^+$ 15 g tungstic acid $WO_3.H_2O$ was heated to about 45° C. in 130 ml of 30% hydrogen peroxide for 24 hours. The solution was cooled down to room temperature and filtered. 22.6 g of picolinic acid was dissolved in 40 ml of water. The tungstic acid solution was cooled with ice to 0° C. and then the dissolved picolinic acid was added. The solution resulting was stirred for 48 hours at room temperature until a white solid was formed which was filtered off. The filtrate was kept at 0° for 48 hours. White crystals were filtered and washed with ether. The collected solid amounted to 16.7 g which corresponds to a 43% yield. Analysis: calculated for $WO_{12}N_3C_{18}H_{17}$: C, 33.18%; H, 2.64%; N, 6.45%; O [active]=9.83%; W, 28.25%. Found: C, 32.82%; H, 2.45%; N, 6.25%; O [active] 9.25%; W, 27.7%. Infrared analysis: [CO]=1735 cm$^{-1}$ [strong], 1690 cm$^{-1}$ [strong]; [O—O]=830 cm$^{-1}$ [strong]; [W=O]=935 cm$^{-1}$ [very strong].

EXAMPLE 15

Preparation of $WO_3$[dipicolinate][$H_2O$]$_2$ 31.0 g tungstic acid $WO_3.H_2O$ was dissolved in 300 ml, of 30% hydrogen peroxide and stirred at about 45° for 20 hours. This solution was cooled to room temperature and filtered. The remaining solution was heated to 45° C. and 15 g dipicolinic acid was added. The solution gradually changed from colorless to a yellow color. The stirring was continued for 4 hours at 45° C. After cooling to room temperature, 17 g of a crystalline yellow solid was filtered and collected (46% yield). Analysis: calculated for $WO_9NC_7H_7$: C, 19.39%; H, 1.62%; N, 3.24%; W, 42.46%. Found: C, 19.34%; H, 1.83%; N, 3.22%; W, 42.21%. Molecular weight calculated 434, found 428 in tetrahydrofuran as a solvent. Infrared analysis: [CO]=1705, 1685 cm$^{-1}$ [very strong]; [OH]=3570 cm$^{-1}$ [medium]; 3480 cm$^{-1}$ [medium]; [O]=870 cm$^{-1}$ [strong]; [W=O]=980 cm$^{-1}$ [strong].

EXAMPLE 16

Preparation of $WO_3$[dipicolinate][$CH_3OH$]$_2$

The complex $WO_3$[dipicolinate][$H_2O$]$_2$ was recrystallized from methanol. The resulting crystals corresponded to complex $WO_3$[dipicolinate][$CH_3OH$]$_2$. Analysis: calculated for $WO_9C_9H_{11}$: C, 23.43%; H, 2.41%; N, 3.06%; W, 39.89%. Found: C, 23.26%; H, 1.83%; N, 3.22%; W, 39.62.

EXAMPLE 17

Preparation of WO$_2$[2,6-bishydroxymethylpyridine bisalcoholate]

3.6 g of tungstic acid WO$_3$.H$_2$O and 2.0 g of 2,6-bishydroxymethylpyridine were mixed and refluxed in 30 ml of water for 13 hr. A 75% yield of the tungsten oxo complex, a greenish color solid, was obtained after filtration, water washing, and drying under vacuum. Analysis calculated for C$_7$H$_7$NO$_4$W: C, 23.82%, H, 2.00%, N, 3.97%, W, 52.08%. Found: C, 23.19%, H, 1.95%, N, 3.66%, W, 49.7%. Infrared analysis: no absorption bands characteristic of [OH], [CO], and [O—O]; [W=O]=7 90 cm$^{-1}$ [strong].

EXAMPLE 18

Oxidation of Allyl Alcohol 2 g allyl alcohol, 40 millimols of 90% aqueous hydrogen peroxide and 0.32 g of [MoO$_5$(picolinate)]$^-$[H$_3$O]$^+$ were diluted with 10 g methanol and then reacted for 22 hours at 80° C. Titration of the resulting solution showed 7.7 millimols of active oxygen corresponding to 19% of hydrogen peroxide left from the original amount employed. The solution was analyzed by gas chromatography with 1,5-pentanediol added as the internal standard and this indicated that the 3.4 g of isomeric monomethyl ethers of glycerol are the only products which were detected. This calculates to a 98% efficiency based on the hydrogen peroxide consumed.

EXAMPLE 19

Oxidation of Allyl Alcohol 2 g allyl alochol, 34.3 millimols of 30% aqueous hydrogen peroxide and 0.41 g of [MoO$_5$(picolinate)]$^-$[H$_3$O]$^+$ were diluted with 10 g methanol and then reacted at 80° C. for 23 hours. The resulting product was titrated for active oxygen and showed that 0.5 millimols of the original hydrogen peroxide were left. Gas chromatographic analysis showed that 1.8 g of the isomeric monomethyl ethers of glycerol were the only detected products. The efficiency of the epoxidation was 52% based on the hydrogen peroxide consumed.

EXAMPLE 20

Oxidation of Allyl Alcohol 2 g allyl alcohol, 32 millimols of 30% aqueous hydrogen peroxide and 0.69 g of [MoO$_5$(picolinate)]$^-$[(picolinic acid)$_2$.H.(H$_2$O)]$^+$ were diluted with methanol and reacted at 80° for 23 hours. Active oxygen was titrated by the iodometric method and this showed that 14.1 millimols of hydrogen peroxide were left. From gas chromatographic analysis, it was concluded that 0.62 g of the isomeric monomethyl ethers of glycerol were the only detected products. The efficiency of the reaction is 30% based on the amount of hydrogen peroxide consumed.

EXAMPLE 21

Oxidation of Allyl Alcohol 2 g allyl alcohol, 32.5 millimols of 30% aqueous hydrogen peroxide and 0.40 g of the catalyst MoO$_3$[dipicolinate].[H$_2$O] were diluted with 10 g methanol and reacted at 80° C. for 6 hours. Active oxygen titration showed that 14.8 millimols of the original amount of hydrogen peroxide employed were left after the reaction. By gas chromatographic analysis, it appeared that 1.19 g of the isomeric monomethyl ethers of glycerol were the only products. The efficiency of the epoxidation was 63.8% based on the amount of hydrogen peroxide consumed.

EXAMPLE 22

Oxidation of Allyl Alcohol

The reactants, 2 g allyl alcohol, 34.5 millimols of 30% aqueous hydrogen peroxide, 0.54 g of the catalyst, WO$_3$[dipicolinate].[H$_2$O]$_2$ were diluted with 10 g methanol and then reacted for 3 hours at 80° C. The active oxygen was titrated and it was determined that 1.88 millimols of the original hydrogen peroxide was left. Through gas chromatographic analysis it was determined that 1.45 g of the isomeric monomethyl ethers of glycerol were the only products of the reaction. The efficiency of this process was calculated to be 42% based on the amount of hydrogen peroxide consumed.

EXAMPLE 23

Oxidation of Cyclohexanone 3 g of cyclohexanone and 0.4 g of the catalyst WO$_3$.[dipicolinate][H$_2$O]$_2$ were diluted with 10 g acetonitrile in a round-bottom flask. 31 millimols of aqueous 90% hydrogen peroxide diluted with acetonitrile was slowly added to the mixture and the reaction proceeded at 80° C. for 22 hours. Then the active oxygen was determined by titration and it was shown that 5.3 millimols of the original hydrogen peroxide was left. By gas chromatography with biphenyl as an internal standard and by NMR analysis, it was found that epsilon caprolactone [0.4 g] and polymeric peroxides were the products of the reaction.

EXAMPLE 24

Oxidation of Cyclohexanone 3 g cyclohexanone, 31 millimols of 90% aqueous hydrogen peroxide and the catalyst, 0.31 g of MoO$_3$[dipicolinate][H$_2$O] were diluted with 10 g methanol and reacted at 60° C. for 24 hours. The titration of active oxygen showed that 4.3 millimols of the hydrogen peroxide initially employed was left at the end. The resulting products were 0.31 g of methyl 6-hydroxyheptanoate, 0.11 g epsilon-caprolactone, 0.27 g of methyl 6-oxohexanoate and a trace of dimethyl adipate as was determined by nuclear magnetic resonance and gas chromatographic analysis.

EXAMPLE 25

Oxidation of 2-Methylcyclohexanone 3 g of 2-methylcyclohexanone, 8.8 millimols of aqueous 90% hydrogen peroxide and 0.3 g of the catalyst [WO$_5$(picolinate)]$^-$[H$_3$O]$^+$ were diluted with 15 ml of methanol and reacted at 80° C. for 3 hours. Active oxygen titration showed that no hydrogen peroxide was left. The resulting products, 0.3 g of methyl 6-oxoheptanonate, 0.5 g of methyl 6-hydroxyheptanoate and polymeric peroxide was determined by nuclear magnetic resonance and gas chromatograhic analysis.

EXAMPLE 26

Oxidation of 2-Methylcyclohexanone 3 g of 2-methylcyclohexanone, 35.3 millimols of 90% aqueous hydrogen peroxide and 0.3 g of the catalyst [MoO$_5$(picolinate)]$^-$[H$_3$O]$^+$ were diluted with 10 g methanol and the solution was allowed to react at 50° C. for 24 hours. At the end of the reaction the active oxygen was determined by titration and no active oxygen was found. The resulting products 5.7 millimols of methyl 6-hydroxyheptanonate, 6.3 millimols of methyl-6-oxoheptanonate and 8.6 millimols of oligomeric peroxides were analyzed and determined by nuclear magnetic resonance and gas chromatography.

EXAMPLE 27

Oxidation of 2-Methylcyclohexanone 1.8 g of 2-methylcyclohexanone, 35 millimols of aqueous 90% hydrogen peroxide and 0.25 g of the catalyst $MoO_3$[dipicolinate].[$H_2O$] were diluted with about 5 g methanol and reacted at 50° C. for 24 hours. Titration for active oxygen showed that about 22 millimols of hydrogen peroxide was left. By gas chromatographic analysis and nuclear magnetic resonance, it was shown that 1.0 g methyl 6-oxoheptanonate and 0.7 g methyl 6-hydroxyheptanonate were obtained. The efficiency of the process based on hydrogen peroxide consumed is 100%.

EXAMPLE 28

Oxidation of Cyclopentanone 2.6 g of cyclopentanone, 29.5 millimols of aqueous 90% hydrogen peroxide and 0.31 g of the catalyst $MoO_3$[dipicolinate].[$H_2O$] were diluted with 10 g methanol and reacted at 60° C. for 24 hours. A titration of active oxygen at the end showed that 4.5 millimols of hydrogen peroxide were left. By gas chromatographic analysis and by nuclear magnetic resonance it was shown that 1 g of methyl 5-hydroxypentanonate was the main product. The efficiency of this process based on hydrogen peroxide consumed was determined to be 39%.

EXAMPLE 29

Oxidation of Cyclopentanone

The reactants 2.6 g cyclopentanone, 36 millimols of 90% aqueous hydrogen peroxide and 0.4 g of $WO_3$[dipicolinate].[$H_2O$]$_2$ were diluted with 10 g acetonitrile and then reacted at 60° C. for 24 hours. A titration for active oxygen showed that 5 millimols of hydrogen peroxide were left. By gas chromatographic analysis and by nuclear magnetic resonance, it was shown that the only product was 0.7 g delta-valerolactone. The efficiency of the present process based on hydrogen peroxide consumed was found to be 23%.

EXAMPLE 30

Oxidation of Cyclopentanone 2.6 g cyclopentanone, 31 millimols of aqueous 90% hydrogen peroxide and 0.31 g of the catalyst $MoO_3$[dipicolinate].[$H_2O$] were diluted with 10 g acetonitrile and the mixture was allowed to react at 60° C. for 24 hours. Then a titration for active oxygen was made and it was shown that 2 millimols of active oxygen were left. By gas chromatographic analysis and by nuclear magnetic resonance it was indicated that 0.8 g of delta-valerolactone was the only product of the reaction. The efficiency of the catalytic oxidation based on the amount of hydrogen peroxide consumed was found to be 28%.

EXAMPLE 31

Oxidation of 2-Methylcyclopentanone 3 g of 2-methylcyclopentanone, 31 millimols of aqueous 90% hydrogen peroxide and 0.31 g of the catalyst $MoO_3$[dipicolinate].[$H_2O$] were diluted with 10 g acetonitrile and reacted at 50° C. for 24 hours. At the end of the reaction 0.43 g biphenyl were added as an internal standard. By gas chromatographic analysis and nuclear magnetic resonance, it was found that 12.7 millimols 5-methyl-delta-valerolactone and about 2 millimols of 5-oxohexanoic acid were the only products. Titration for active oxygen showed that 3.4 millimols of hydrogen peroxide remained after the reaction. The efficiency of the reaction based on the amount of hydrogen peroxide consumed was found to be 52.5%.

EXAMPLE 32

Oxidation of 2-Phenylcyclohexanone 2.7 g of 2-phenylcyclohexanone, 15 millimols of aqueous 90% hydrogen peroxide and 0.17 g of the catalyst $MoO_3$[dipicolinate].[$H_2O$] were diluted with 10 g methanol and reacted 50° C. for 24 hours. Determination of active oxygen by titration at that time showed that 0.3 millimols of hydrogen peroxide were left after the reaction. Gas chromatographic analysis and nuclear magnetic resonance showed that the major products of the reaction were 1.1 g of methyl 6-phenyl-6-oxohexanoate and 0.3 g of methyl 6-phenyl-6-hydroxy-hexanoate. The efficiency of the oxidation based on the amount of hydrogen peroxide consumed was determined to be 77%.

EXAMPLE 33–47

Stoichiometric Oxidation of Alcohols 0.0658 g of 2-octanol, 0.0662 g of trichloroethylene and 0.6 g of $CD_3OD$ were combined in a sample vial. 0.1036 g [$WO_5$(picolinate)]$^-$[$H_3O$]$^+$ were added to the solution and the resulting mixture was agitated until a homogeneous solution was obtained. The solution was then transferred to an NMR tube and frozen with liquid nitrogen and sealed under vacuum. The sealed tube was heated at 50° C. in a constant temperature silicon oil bath for the desired length of time with the reaction monitored by NMR (nuclear magnetic resonance). After the reaction was completed, the tube was opened and the contents of the tube analyzed by gas chromatography in order to assure that the yield calculated from the nuclear magnetic resonance was correct. Both the yield as analyzed according to nuclear magnetic resonance and gas chromatography were essentially equivalent. The examples 33-47 performed are listed in Table 1.

TABLE 1

| Ex. | Complex (m moles) | T C.° | Time hr. | Solvent | Secondary Alcohol | Initial m moles | Final m moles | Conversion | m moles of ketone / m moles of metal |
|---|---|---|---|---|---|---|---|---|---|
| 33 | [$MoO_5$(picolinate)]$^-$[$H_3O$]$^+$ (.266) | 50° C. | 29 | $CD_3OD$ | 2-octanol | .473 | .118 | 75% | .134 |
| 34 | $MoO_5$(HMPA)($H_2O$) (.251) | 50° C. | 40 | $CD_3OD$ | 2-octanol | .525 | .436 | 17% | .356 |
| 35 | $MoO_5$(HMPA) (.253) | 50° C. | 73 | $CDCl_3$ | 2-octanol | .522 | .402 | 23% | .47 |
| 36 | $MoO_5$(HMPA) | 50° C. | 41 | $CD_3CN$ | 2-octanol | .529 | .434 | 18% | .37 |

TABLE 1-continued

| Ex. | Complex (m moles) | T C.° | Time hr. | Solvent | Secondary Alcohol | Initial m moles | Final m moles | Conversion | m moles of ketone / m moles of metal |
|---|---|---|---|---|---|---|---|---|---|
| 37 | [MoO5(picolinate)]⁻ [(picolinic acid)₂ . H . H₂O]⁺ (.255) (.254) | 50° C. | 47 | CD₃OD | 2-octanol | .531 | .334 | 37% | .77 |
| 38 | [WoO5(picolinate)⁻ . [(methyl picolinate) . H]⁺ (.250) | 50° C. | 24 | CD₃OD | 2-octanol | .497 | .410 | 17.5% | .348 |
| 39 | [WO5(picolinate)]⁻[H₃O]⁺ (.256) | 50° C. | 18 | CD₃OD | 2-octanol | .505 | .167 | 67% | 1.32 |
| 40 | WO5(HMPA)(H₂O) (.294) | 50° C. | 47 | CD₃OD | 2-octanol | .529 | .423 | 20% | .36 |
| 41 | [WO5(picolinate)]⁻[H₃O]⁺ (.249) | 50° C. | 23 | CD₃OD | cyclohexanol | .495 | — | 58% | 1.15 |
| 42 | [MoO5(picolinate)]⁻[H₃O]⁺ (.237) | 50° C. | 29 | CD₃OD | cyclohexanol | .562 | .334 | 40% | .783 |
| 43 | [MoO5(picolinate)]⁻[H₃O]⁺ (.227) | 50° C. | 102 | CD₃OD | phenethyl | .51 | .087 | 83% | 1.86 |
| 44 | [MoO5(picolinate)]⁻[H₃O]⁺ (.252) | 50° C. | 40 | CD₃OD | phenethyl | .495 | .109 | 78% | 1.53 |
| 45 | [WO5(picolinate)]⁻[H₃O]⁺ (.257) | 50° C. | 17 | CD₃OD | phenethyl | .535 | .161 | 70% | 1.454 |
| 46 | [MoO5(picolinate)]⁻[H₃O]⁺ (.251) | 50° C. | 63 | CD₃OD | 6-hydroxyheptanoic acid methyl ester | .542 | .244 | 55% | 1.19 |
| 47 | [WO5(picolinate)]⁻[H₃O]⁺ (.252) | 50° C. | 23 | CD₃OD | 6-hydroxyheptanoic | .513 | .130 | 74.6% | 1.52 |

EXAMPLE 48-53

Oxidation of Secondary Alcohols 0.2363 g of 2-octanol, 0.0463 g of hydrogen peroxide in CD₃OD, and 0.2306 g of trichloroethylene were combined in a sample vial and a catalytic amount of 0.0045 g of [WO₅ (picolinic acid)]⁻. [H₃O]⁺ were added. The resulting solution was agitated briefly and then 0.2 ml of CD₃OD was added to assure all of the catalyst was in solution when transferred to the nuclear magnetic resonance tube. The sealed tube was heated at 80° C. in a constant temperature bath for the indicated time with the reaction monitored by nuclear magnetic resonance. At the end of the run, the tube was opened and then the resulting product was analyzed by gas chromatography. Both the yields determined by either NMR or gas chromatography were essentially equivalent. The examples 48-53 of catalytic oxidation of secondary alcohols are listed in Table 2.

EXAMPLE 54

Preparation of a Supported Catalyst

Supported catalysts are prepared by adding a solid support into a solution or suspension of the appropriate amount of the catalyst.

A zeolite diatomateous silica distributed by Johns Manville Corp. was flux calcined by Analab Corp. and sold as Chromosorb WHP for high performance. The Chromosorb WHP was then added to a solution of a catalyst, e.g. peroxo tungsten dipicolinate in a solvent such as acetonitrile. The resulting slurry was then rotary evaporated at room temperature and then evacuated by high vacuum pumping.

EXAMPLES 55-63

Oxidation of Cyclohexanone with H₂O₂ Using Supported Catalysts

A weighed amount of the supported catalyst prepared according to Example 54 was then introduced into a tubular gas phase reactor. Hydrogen peroxide was dissolved in cyclohexanone and then passed over the supported catalyst at an appropriate temperature with helium or argon as carrier gas. In Example 55, 44 mg of a 1% WO₃ [dipicolinate][H₂O]₂ on Chromosorb WHP supported catalyst was placed in a 8 mm diameter glass tubing. This tubing served as reactor and was on line connected to a gas liquid chromatographic separation and detection unit. For test and demonstration purposes this is most easily arranged by adapting the injector part of a gas liquid chromatography instrument as the reactor. A 20 microliter of solution of the reagents and of a gas liquid chromatography standard (e.g. 3 g of cyclohexanone, 3.65 g of 30% H₂O₂ in acetonitrile, 0.4012 g biphenyl as gas liquid chromatographic standard, and further diluted with 10 ml of acetonitrile) was injected into the reactor which is temperature regulated and set to e.g. about 200° C. The contact time was less than 0.1 sec. On line gas liquid chromatography analysis showed unreacted ketone and the reaction product caprolactone.

The 20 microliters of reagent solution resulted in 4.77×10⁻³ m moles of caprolactone formed. This corresponds to a 17% conversion of the injected cyclohexanone to caprolactone and a catalyst turnover number of 4.7 for this one injection. The "catalyst activity time tested" (Table III) represents the length of time that the particular supported catalyst was tested for the reaction by repeated injection of the reactants.

Similarly, as set forth in Examples 55-63 of Table III, various supported catalysts were prepared and tested for the catalytic conversion of cyclohexanone to caprolactone using H₂O₂.

EXAMPLES 64-65

Oxidation of cyclohexanone with H₂O₂ using supported catalysts

The process of this example is similar to that employed in examples 55-63. The catalysts were MoO₃ (diethylenetriamine) and molybdenum trioxide.

The reactor temperature in this case was at 150° C. which is lower than the reactor temperature of Example 55-63.

TABLE 2

Oxidation of Secondary Alcohols by $H_2O_2$ Catalyzed by Peroxo Complexes

| Example | Complex (m moles) | C.° | Time hr. | $H_2O_2$ (m moles) | Alcohol (m moles) | Solvent | Yield % | No. of metal Turnover |
|---|---|---|---|---|---|---|---|---|
| 48 | [WO$_5$ (picolinate)]$^-$[H$_3$O]$^+$ (0.060) | 80° C. | 18 | 1.83 | 2-octanol (1.81) | CD$_3$OD | 70 | 21 |
| 49 | '' (0.060) | 80° C. | 4½ | 1.81 | Methyl 6-hydroxyheptanoate (1.77) | CD$_3$OD | 48 | 15.3 |
| 50 | '' (0.061) | 80° C. | 1½ | 1.94 | Phenetyl (1.79) | CD$_3$OD | 48 | 14.1 |
| 51 | '' (0.053) | 80° C. | 4¼ | 1.80 | Cyclohexanol (1.82) | CD$_3$OD | 50 | 17.2 |
| 52 | WO$_3$[dipicolinate][CH$_3$OH]$_2$ | 80° C. | 5½ | 49.9 | 2-octanol (99.3) | CH$_3$CN | 97 | 48.4 |
| 53 | '' (1.00) | 80° C. | 5½ | 50 | Cyclohexanol (100) | CH$_3$CN | 71 | 35.5 |

Table III

| Example | Catalyst (Wt: mmol) | Conversion/pass (%) | Cat.t.o #/pass of 20μ 1 reactant solution | Cat. Activity time tested (hr) |
|---|---|---|---|---|
| 55 | WO$_3$[dipicolinate][H$_2$O]$_2$ 4.4 × 10$^{-4}$g: 1.1 × 10$^{-3}$ | 17 | 4.7 | 2 |
| 56 | MoO$_3$[dipicolinate][H$_2$O] 4.6 × 10$^{-4}$g: 1.1 × 10$^{-3}$ | 3 | 1.1 | 2.5 |
| 57 | WO$_2$[2,6-bishydroxymethylpyridine bisalcoholate] 7.92 × 10$^{-4}$g: 2.24 × 10$^{-3}$ | 0.8 | 0.1 | 6 |
| 58 | no catalyst | 0 | 0 | — |
| 59 | MoO$_2$[2,6-bishydroxymethylpyridine bisalcoholate] 5.3 × 10$^{-4}$g: 1.3 × 10$^{-3}$ | 10 | 2.2 | 1.5 |
| 60 | [MoO$_5$(picolinate)]$^-$[H$_3$O]$^+$ 4.3 × 10$^{-4}$g: 1.0 × 10$^{-3}$ | 15 | 4.1 | 1.5 |
| 61 | MoO$_5$[HMPA][H$_2$O] 5.0 × 10$^{-4}$g: 1.2 × 10$^{-3}$ | 23 | 5.6 | 1.5 |
| 62 | MoO$_2$[acetylacetone]$_2$ 4.7 × 10$^{-4}$g: 1.1 × 10$^{-3}$ | 14 | 3.6 | 1.5 |
| 63 | [MoO$_5$(picolinate)]$^-$ [(picolinic acid)$_2$ · H(H$_2$O)]$^+$ 5.2 × 10$^{-4}$g: 1.3 × 10$^{-3}$ | 12 | 2.8 | 1.5 |
| 64 | MoO$_3$(diethylenetriamine) 7.94 × 10$^{-4}$g; 3.21 × 10$^{-3}$ | 4.4 | 0.5 | 6 |
| 65 | Molybdenum trioxide 7.50 × 10$^{-4}$g; 5.20 × 10$^{-3}$ | 14.9 | 1.2 | 3 |

EXAMPLE 66

Oxidation of cyclohexanone with $H_2O_2$ Using Supported Catalysts

A reaction using 30% aqueous $H_2O_2$ solution (instead of the 30% $H_2O_2$ solution in acetonitrile) as the oxidant, but otherwise as described for example 55 of Table 2, resulted in a 8% cyclohexanone to caprolactone conversion/pass and a catalyst turnover of 3.

EXAMPLES 67 and 68

Oxidation of Cyclohexanone with $H_2O_2$ Using Support Catalysts

Examples similar to Example 55–63 were conducted using 5% supported catalysts prepared in the manner described above and with the reaction run at different temperatures. Thus, for this series a 1 microliter solution of 1.00 g of cyclohexanone, 1.43 g of 28.5% $H_2O_2$ in acetonitrile, 0.177 g of biphenyl and diluted with 5 ml acetonitrile, was allowed to react in the manner described above in the tubular reactor. The results for WO$_3$[dipicolinate]·[H$_2$O]$_2$ and for MoO$_3$[dipicolinate][H$_2$O] are summarized in Table IV. The employment of various controlled reaction temperatures allows the relationship between relative yield of lactone and reaction temperature to be determined.

Table IV

| Example | Catalyst[a] | Temperature (°C.) | Yield (%) |
|---|---|---|---|
| 67 | MoO$_3$[dipicolinate][H$_2$O] 0.0774g | 150 | 25 |
| | | 200 | 44 |
| 68 | WO$_3$[dipicolinate][H$_2$O]$_2$ 0.0789g | 100 | 13 |
| | | 125 | 45 |
| | | 150 | 50 |
| | | 200 | 45 |

[a]5% catalyst supported on Chromosorb WHP

EXAMPLE 69

Oxidation of Cyclohexanone With $H_2O_2$ Using Supported Catalysts

This example relates to a larger scale oxidation of cyclohexanone to caprolactone. 0.301 g of 1% WO$_3$[dipicolinate][H$_2$O]$_2$ supported on Chromosorb WHP was placed in a tubular reactor and secured by a thin layer of quartz chips. The reactor was heated to 200° C. with a flow of argon at 15 ml/min. A reactant solution consisting of 3 g of cyclohexanone, 4 g of 30% $H_2O_2$ in acetonitrile, and 10 ml of acetonitrile was added slowly into the heated reaction zone. After the addition was completed, the crude product solution was determined by gas liquid chromatographic methods to contain caprolactone and cyclohexanone. The iodine-starch test also indicated the presence of unreacted peroxidic material. The mixture was evaporated, diluted with water, and extracted with chloroform. The chloroform layers were again evaporated. Proton NMR of the resulting residue indicated the presence of caprolactone and cyclohexanone. Addition of NMR internal standard (trichloroethylene) indicated 0.25 g of caprolactone, i.e., 8% conversion of cyclohexanone with a catalyst turnover number (t.o.) of 314.

EXAMPLE 70

Oxidation of Cyclohexanone With $H_2O_2$ Using Supported $MoO_3$-[dipicolinate][$H_2O$]

This is a larger scale example like Example 69 employing 5% $MoO_3$[dipicolinate][$H_2O$] supported on Chromosorb WHP as described above. Simultaneous addition of $H_2O_2$ solution in acetonitrile and a separate solution of cyclohexanone in acetonitrile was used. The temperature of reaction was regulated between 180°–200° C. 0.015 g of 5% of supported catalyst was used. The reactants were 3 ml of 28.5% $H_2O_2$ in acetonitrile and 2.5 g of cyclohexanone in acetonitrile. With an argon flow of 20 ml/min as the carrier gas, the addition of the reactants took 0.3 hrs. Conversion of ketone to caprolactone was 6.4% with a catalyst turnover of 28.

EXAMPLE 71

Oxidation of Cyclohexanone With $H_2O_2$ Using Supported $WO_3$[dipicolinate][$H_2O$]$_2$ This is a larger scale example and differs from Example 70 by employing the analogous tungsten catalyst.

0.017 g of 5% $WO_3$[dipicolinate][$H_2O$]$_2$ was used as a supported catalyst. A solution of $H_2O_2$ in acetonitrile and a separate solution of cyclohexanone in acetonitrile were simultaneously introduced into the reaction zone. 3 ml of 28.5% $H_2O_2$ in acetonitrile and 2.5 g of cyclohexanone in acetonitrile were employed.

The carrier gas was provided by an argon flow of 20 ml/min and the addition of the reactants took 0.3 hours. A 4.6% conversion of cyclohexanone to caprolactone was observed with a catalyst turnover of 23.

We claim:

1. In a process for oxidation of alicyclic ketones to lactones, ω-hydroxy acids and esters wherein the oxidizing agent is hydrogen peroxide and the oxidation is catalyzed by a peroxo complex of molybdenum or tungsten, the improvement which comprises employing a peroxo complex soluble in the oxidation reaction mixture wherein molybdenum or tungsten atoms are connected to a complexing aza heterocyclic aromatic compound having carboxylic acid group on a carbon atom which is in α-position relative to the aza nitrogen.

2. Improved process for oxidation as set forth in claim 1 wherein a cyclic ketone is oxidized using as reaction medium an inert solvent whereby the product is a lactone.

3. Improved process for oxidation as set forth in claim 1 wherein a cyclic ketone is oxidized using as reaction medium water, whereby the product is an omega-hydroxy acid.

4. Improved process for oxidation as set forth in claim 1 wherein a cyclic ketone is oxidized using as a reaction medium an alcohol, whereby the product is an ester of an omega-hydroxy acid.

5. Improved process for oxidation as set forth in claim 1 wherein the complexing aza heterocyclic aromatic compound is picolinic or dipicolinic acid.

6. Improved process for oxidation as set forth in claim 1 wherein the catalyst is supported by a catalyst carrier.

7. In a process for oxidation of alicyclic ketones using as reaction medium an inert solvent and wherein the reaction products are lactones, the improvement which comprises catalyzing an oxidation by hydrogen peroxide by a covalent peroxo complex of molybdenum or tungsten.

8. Improved process for oxidation as set forth in claim 7 wherein the catalyst is supported by a catalyst carrier.

9. Improved process for oxidation as set forth in claim 8 wherein an oxo complex of molybdenum or tungsten known to be transformable to a peroxo complex with hydrogen peroxide is impregnated on the catalyst carrier for forming a peroxo complex when contacted with hydrogen peroxide.

10. Improved process for oxidation as set forth in claim 7 wherein the ketone reacts from the gas phase.

11. Improved process of oxidation of ketones as set forth in claim 7 wherein the covalent peroxo complex of molybdenum or tungsten comprises an aza-metal bond.

12. Improved process for oxidation of ketones as set forth in claim 7 wherein the covalent peroxo complex of molybdenum or tungsten comprises a metal carboxylate bond.

13. Improved process for oxidation of ketones as set forth in claim 7 wherein the covalent peroxo complex of molybdenum or tungsten comprises picolinates or dipicolinates.

14. Improved process for oxidation of ketones as set forth in claim 7 comprising dissolving the ketone and the catalyst in a mutually inert solvent.

15. In a process for oxidation of alicyclic ketones using as reaction medium water and wherein the reaction products are omegahydroxy acids, the improvement which comprises catalyzing an oxidation by hydrogen peroxide by a covalent peroxo complex of molybdenum or tungsten.

16. Improved process for oxidation as set forth in claim 15 wherein the catalyst is supported by a catalyst carrier.

17. Improved process for oxidation as set forth in claim 16 wherein an oxo complex of molybdenum or tungsten known to be transformable to a peroxo complex with hydrogen peroxide is impregnated on the catalyst carrier for forming a peroxo complex when contacted with hydrogen peroxide.

18. Improved process for oxidation as set forth in claim 15 wherein the ketone reacts from the gas phase.

19. Improved process of oxidation ketones as set forth in claim 15 wherein the covalent peroxo complex of molybdenum or tungsten comprises an aza-metal bond.

20. Improved process for oxidation of ketones as set forth in claim 15 wherein the covalent peroxo complex of molybdenum or tungsten comprises a metal carboxylate bond.

21. Improved process for oxidation of ketones as set forth in claim 15 wherein the covalent peroxo complex of molybdenum or tungsten comprises picolinates or dipicolinates.

22. In a process for oxidation of alicyclic ketones using as reaction medium an alcohol, and wherein the reaction products are esters of omega-hydroxy acids, the improvement which comprises catalyzing an oxidation by hydrogen peroxide by a covalent peroxo complex of molybdenum or tungsten.

23. Improved process for oxidation as set forth in claim 22 wherein the catalyst is supported by a catalyst carrier.

24. Improved process for oxidation as set forth in claim 23 wherein an oxo complex of molybdenum or tungsten known to be transformable to a peroxo complex with hydrogen peroxide is impregnated on the catalyst carrier for forming a peroxo complex when contacted with hydrogen peroxide.

25. Improved process for oxidation as set forth in claim 22 wherein the ketone reacts from the gas phase.

26. Improved process of oxidation of ketones as set forth in claim 22 wherein the covalent peroxo complex of molybdenum or tungsten comprises an aza-metal bond.

27. Improved process for oxidation of ketones as set forth in claim 22 wherein the covalent peroxo complex of molybdenum or tungsten comprises a metal carboxylate bond.

28. Improved process for oxidation of ketones as set forth in claim 22 wherein the covalent peroxo complex of molybdenum or tungsten comprises picolinates or dipicolinates.

29. In a process for oxidation of alicyclic ketones to lactones the improvement which comprises contacting the alicyclic ketones with hydrogen peroxide in the presence of a covalent peroxo complex of molbydenum or tungsten.

30. In a process for oxidation of alicyclic ketones to lactones, $\omega$-hydroxy acids and esters wherein the oxidizing agent is hydrogen peroxide and the oxidation is catalyzed by a peroxo complex of molybdenum or tungsten, the improvement which comprises employing a peroxo complex wherein molybdenum or tungsten atoms connected to a complexing aza heterocyclic compound having a carboxylic acid group on a carbon atom which is in $\alpha$-position relative to the aza nitrogen are supported on a catalyst carrier.

31. Improved process for oxidation as set forth in claim 30 wherein the complexing aza heterocyclic compound is picolinic or dipicolinic acid.

* * * * *